United States Patent [19]

Sosnowski et al.

[11] Patent Number: 4,911,148

[45] Date of Patent: Mar. 27, 1990

[54] DEFLECTABLE-END ENDOSCOPE WITH DETACHABLE FLEXIBLE SHAFT ASSEMBLY

[75] Inventors: Stephen A. Sosnowski, Oceanside; Nadhir B. Kosa; Steven W. Kovalcheck, both of San Diego; John H. Parrish, La Jolla, all of Calif.

[73] Assignee: Intramed Laboratories, Inc., San Diego, Calif.

[21] Appl. No.: 323,304

[22] Filed: Mar. 14, 1989

[51] Int. Cl.$^4$ .............................................. A61B 1/06
[52] U.S. Cl. .......................................... 128/6; 128/4; 128/7
[58] Field of Search ................................... 128/4, 6, 7

[56] References Cited

U.S. PATENT DOCUMENTS

| | | | |
|---|---|---|---|
| 3,788,304 | 1/1974 | Takahashi | 128/6 |
| 4,353,358 | 10/1982 | Emerson | 128/4 |
| 4,577,621 | 3/1986 | Patel | 128/4 |
| 4,580,551 | 4/1986 | Siegmund et al. | 128/4 |
| 4,653,476 | 3/1987 | Bonnet | 128/4 |

Primary Examiner—William H. Grieb
Attorney, Agent, or Firm—Freilich, Hornbaker & Rosen

[57] ABSTRACT

An endoscope having a deflectable tip configured so as to have a small outer diameter of approximately 0.15 inch or less. The endoscope includes a flexible shaft subassembly comprised of a conduit having a deflectable end segment at its distal end which can be controlled by a manually operable mechanism on a handle subassembly. The shaft subassembly further includes a cone subassembly at its proximal end including means for structurally connecting to the handle subassembly. Illumination fibers, an imaging fiber, a pull wire and a working channel extend through the shaft subassembly from its distal end to terminals in the cone subassembly for interfacing to the handle subassembly. The handle subassembly comprises an optical component which allows for the viewing of an image emanating from the shaft subassembly imaging fiber, a deflection mechanism which incorporates a means for physical attachment and axial displacement of the shaft subassembly pull wire, and a locking mechanism for attaching the shaft subassembly to the handle subassembly.

16 Claims, 14 Drawing Sheets

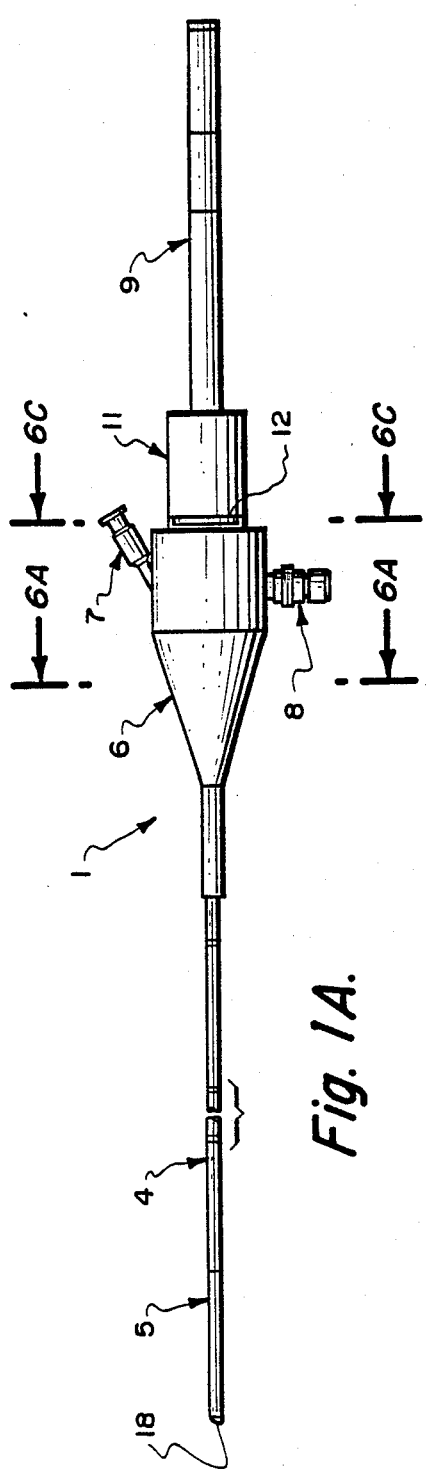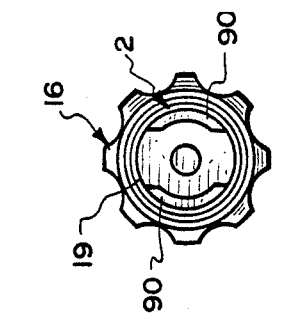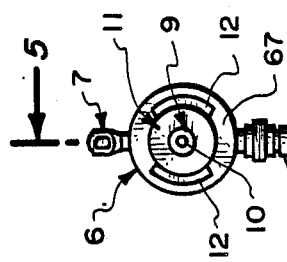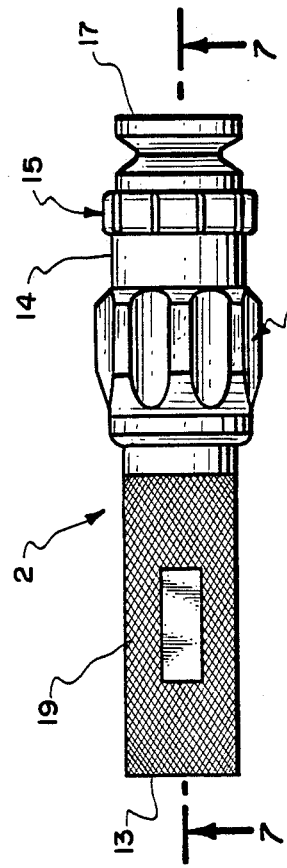

DEFLECTABLE-END ENDOSCOPE WITH DETACHABLE FLEXIBLE SHAFT ASSEMBLY

BACKGROUND OF THE INVENTION

This invention relates generally to endoscopes and more particularly to such instruments which have a flexible shaft and a deflectable end portion controlled via a mechanism at the proximal end.

Endoscopes are used in various medical and industrial applications for viewing unaccessible interior features of cavities, tubes or conduits, such as body organs. The present invention is particularly concerned with endoscopes of flexible and small outside diameter shafts of less than 0.15 inch, useful, for example, as ureteroscopes, hysteroscopes, angioscopes, choledochoscopes, and cystoscopes.

The prior art is replete with endoscopes which incorporate an end portion which can be deflected, by a user, via a control mechanism at the proximal end of the device. Such endoscopes are characterized by various structural configurations which enable a user to control the deflection of the distal tip of the end portion through an angle from approximately 0 degrees to 180 degrees. The following patents are examples of endoscopes having a deflectable tip:

| | |
|---|---|
| 4,653,476 | Bonnet |
| 4,580,551 | Siegmund |
| 4,577,621 | Patel |
| 4,353,358 | Emerson |
| 3,788,304 | Takahashi |

Other structures are shown in the following additional patents:

| | | | |
|---|---|---|---|
| 3,426,663 | 3,948,251 | 4,483,326 | 4,616,630 |
| 3,470,876 | 4,063,796 | 4,503,842 | 4,617,915 |
| 3,572,325 | 4,066,070 | 4,503,843 | 4,630,598 |
| 3,610,231 | 4,175,545 | 4,543,090 | 4,633,882 |
| 3,726,272 | 4,176,662 | 4,557,253 | 4,646,722 |
| 3,788,304 | 4,178,920 | 4,557,254 | 4,650,467 |
| 3,799,150 | 4,203,430 | 4,561,427 | 4,651,202 |
| 3,799,151 | 4,245,624 | 4,566,437 | 4,651,718 |
| 3,856,000 | 4,271,845 | 4,567,882 | 4,653,476 |
| 3,880,148 | 4,277,168 | 4,557,621 | 4,676,228 |
| 3,892,228 | 4,294,233 | 4,586,923 | 4,685,449 |
| 3,897,775 | 4,446,444 | 4,593,680 | 4,686,963 |
| 3,915,157 | 4,447,227 | 4,601,705 | |

SUMMARY OF THE INVENTION

The present invention is directed to an improved endoscope having a deflectable tip configures so as to have a small outer diameter of approximately 0.15 inch or less.

More specifically, the present invention is directed to a flexible shaft subassembly comprised of a conduit having a deflectable end segment at its distal end which can be controlled by a manually operable mechanism on a handle subassembly. The shaft subassembly further includes a cone subassembly at its proximal end including means for structurally connecting to the handle subassembly. Illumination fibers, an imaging fiber, a pull wire and a working channel extend through the shaft subassembly from its distal end to terminals in the cone subsubassembly for interfacing to the handle subassembly. A preferred handle subassembly comprises an optical component which allows for the viewing of an image emanating from the shaft subassembly imaging fiber, a deflection mechanism which incorporates a means for physical attachment and axial displacement of the shaft subassembly pull wire, and a locking mechanism for attaching the shaft subassembly to the handle subassembly.

In accordance with one aspect of the present invention, a series of discrete substantially aligned cutouts are formed in the body of the shaft subassembly end segment. The geometry of the cutouts vary progressively along the length of this deflectable end segment to produce a gradual distal tip deflection profile as the end segment is forced to bend by an axial force on the pull wire. The cutouts are preferably of substantially triangular shape in a plane containing the pull wire and imaging fiber.

In accordance with a preferred embodiment of the invention, the body of the deflectable end segment is comprised of an elongated flexible multi-lumen body covered tightly with a smooth, thin elastomeric sheath. The individual lumens in the body provide passageways for the illumination and imaging fibers, pull wire and a relatively large working channel useful for movement of fluids and/or for passing diagnostic or therapeutic instruments.

In accordance with a preferred embodiment, the conduit connecting the deflectable end portion to the cone subassembly comprises an elongated flexible conduit formed of two elongated counter wrapped flat ribbon coils covered wit an elastomeric sheath over their entire axial length. This conduit configuration provides protection for the encased illumination and imaging fibers and working channel against stresses resulting from the flexure, tension or compression imposed upon the shaft subassembly during operation of the endoscope.

In accordance with still a further aspect of the preferred embodiment, the handle subassembly provides a means to mate with the shaft subassembly and form the complete endoscope unit. Contained within the handle subassembly are: the means to align and optically mate the shaft subassembly imaging fiber bundle with a viewing optics and a focusing mechanism which can be adjusted through the rotation of a screw mechanism; the means for securing the pull wire contained in the shaft subassembly to a component whose axial movement is controlled by the rotation of a screw mechanism; and a means for securely locking the cone subassembly to the handle subassembly in fixed orientation, e.g. via a bayonet mount, whereby the flexure of the deflectable distal end segment is in a plane oriented perpendicular to a plane defined by a working channel port and light post on the cone subassembly.

In accordance with still a further aspect of the preferred embodiment, the shaft subassembly and handle subassembly are provided with watertight seals at all externally exposed mating interfaces to prevent a compromise of internal components resulting from usage and sterilizations.

BRIEF DESCRIPTION OF THE DRAWINGS

FIGS. 1A and 1B are respectively side elevation views of the mating shaft subassembly and handle subassembly of the endoscope in accordance with the present invention. shaft subassembly and handle subassembly of FIGS. 1A and 1B.

DESCRIPTION OF THE PREFERRED EMBODIMENT

Figure 1E:
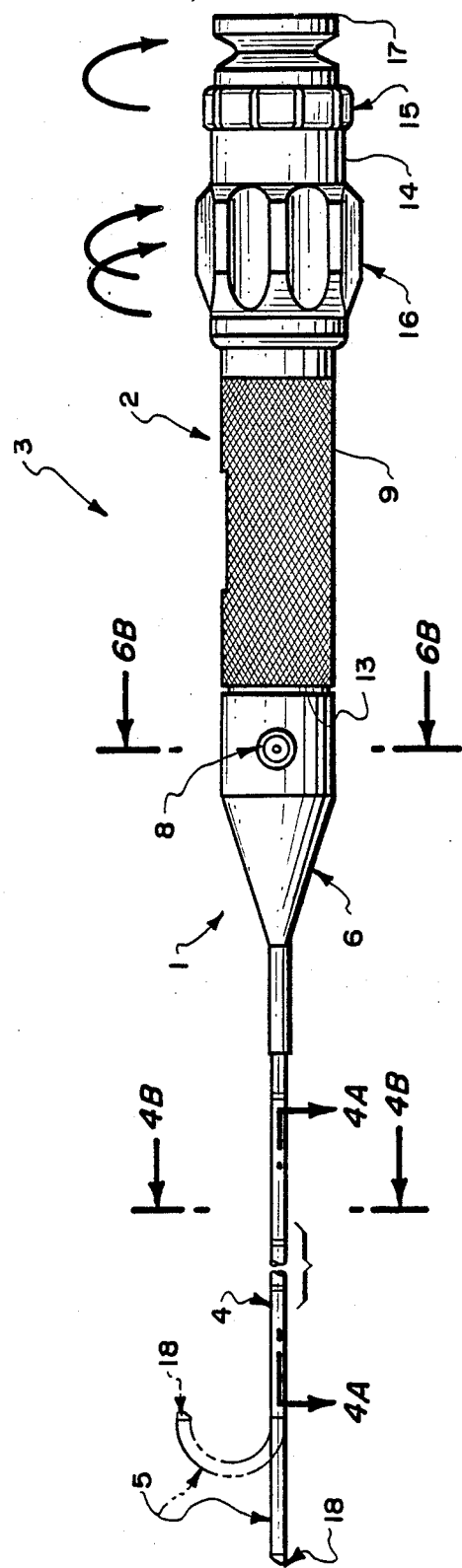
FIG. 1E is a side elevation view of the mated shaft and handle subassemblies in accordance with the present invention.

Attention is initially directed to FIGS. 1A and 1B which respectively illustrate a shaft subassembly 1 and a handle subassembly 2 which mate together to form a complete endoscope 3 as depicted in FIG. 1E. Although endoscope 3 as illustrated in the drawing is particularly configured for use as a ureteroscope, it should be understood that the features of the invention are also applicable to endoscopes configured for other applications. Briefly, the endoscope 3 is comprised of two primary subassemblies; namely a shaft subassembly 1 and a handle subassembly 2 which can be readily operatively attached to each other. The handle subassembly 2, normally held in the grip of a user, has a rigid structure with moveable controls while the shaft subassembly 1, which is partially inserted into a cavity e.g. a human organ, has a smooth flexible structure.

The shaft subassembly 1 in accordance with the invention is basically comprised of an elongated flexible conduit 4 having a deflectable end segment 5 at its distal end and a rigid cone subassembly 6 at its proximal end. The shaft subassembly 1 internally contains elongated illumination fibers, an imaging fiber, a pull wire and a working channel (not shown in FIGS. 1A-1E) to be discussed hereinafter. All of these elongated elements terminate in the cone subassembly 6. The cone subassembly 6 includes a working channel port 7, configured with a female luer fitting, standard in the medical industry for allowing connection of syringes and other tubing adapters to the internal working channel The fitting is preferably angled with respect to the longitudinal axis of the shaft subassembly for ease of insertion of the diagnostic and/or therapeutic instruments. The subassembly 6 further includes a lightpost 8 preferably comprising an industry standard male terminal having a fine polished end face for coupling a light source to the internal illumination fibers. An imaging fiber bundle extends through the rigid post 9 and is terminated at its end by a small ferrule 10. A pull wire is guided through the inner parts of the cone subassembly and is securely attached to a lifter 11 which can be axially translated to deflect the end segment 5 depicted in phantom in FIG. 1E. The cone subassembly 6 also includes a male bayonet connector 12 configured around the lifter 11, for interconnection with a female bayonet connector mounted at the distal end 13 of the handle subassembly 2.

The handle subassembly 2 comprises a cylindrical body which contains an eyepiece 14 configured in a focusing ring 15 which rotates around the central axis of the handle subassembly, and a deflection control ring 16. The deflection control ring 16 is an internally threaded mechanism which rotates from a null position (corresponding to an axially aligned, zero deflection orientation of the distal end segment 5). As the ring 16 is rotated in one direction, it axially translates the lifter 11 to pull the internal pull wire to gradually deflect the distal tip 18 of the end segment 5. The distal tip 18 can operatively be placed at an angle between 0 degrees to 180 degrees with respect to the axis of conduit 4. If the deflection control ring 16 is rotated to any position the deflected distal tip 18 will remain at that position until the deflection control ring 16 is rotated again. The distal end 13 of the handle subassembly 2 is internally terminated with a hollow female bayonet connector which tightly mates with its male counterpart 12 on the cone subassembly 6 when coupled together by a user. The central portion of the proximal end 17 of the eyepiece 14 is configured with a optical window for viewing the image emanating from the imaging fiber bundle at ferrule 10.

Coupling the shaft subassembly 1 to the handle subassembly 2, is initiated by holding in one hand, the handle subassembly around the knurled portion 19 and resetting the deflection control ring 16 to its null deflection position. With the shaft subassembly 1 held in the other hand with proper orientation, the rigid rod 9 is inserted through the opening at the distal end 13 of the handle subassembly 2. To engage the two connectors, the male and female bayonet connectors of the two subassemblies are mated together and the shaft subassembly is rotated with respect to the handle subassembly or vice versa until it locks The two units will then be securely coupled and ready for use. To disconnect the shaft subassembly, rotate the deflection ring to the null deflection position and reverse the direction of rotation of the shaft subassembly with respect to the handle subassembly.

Figure 2:
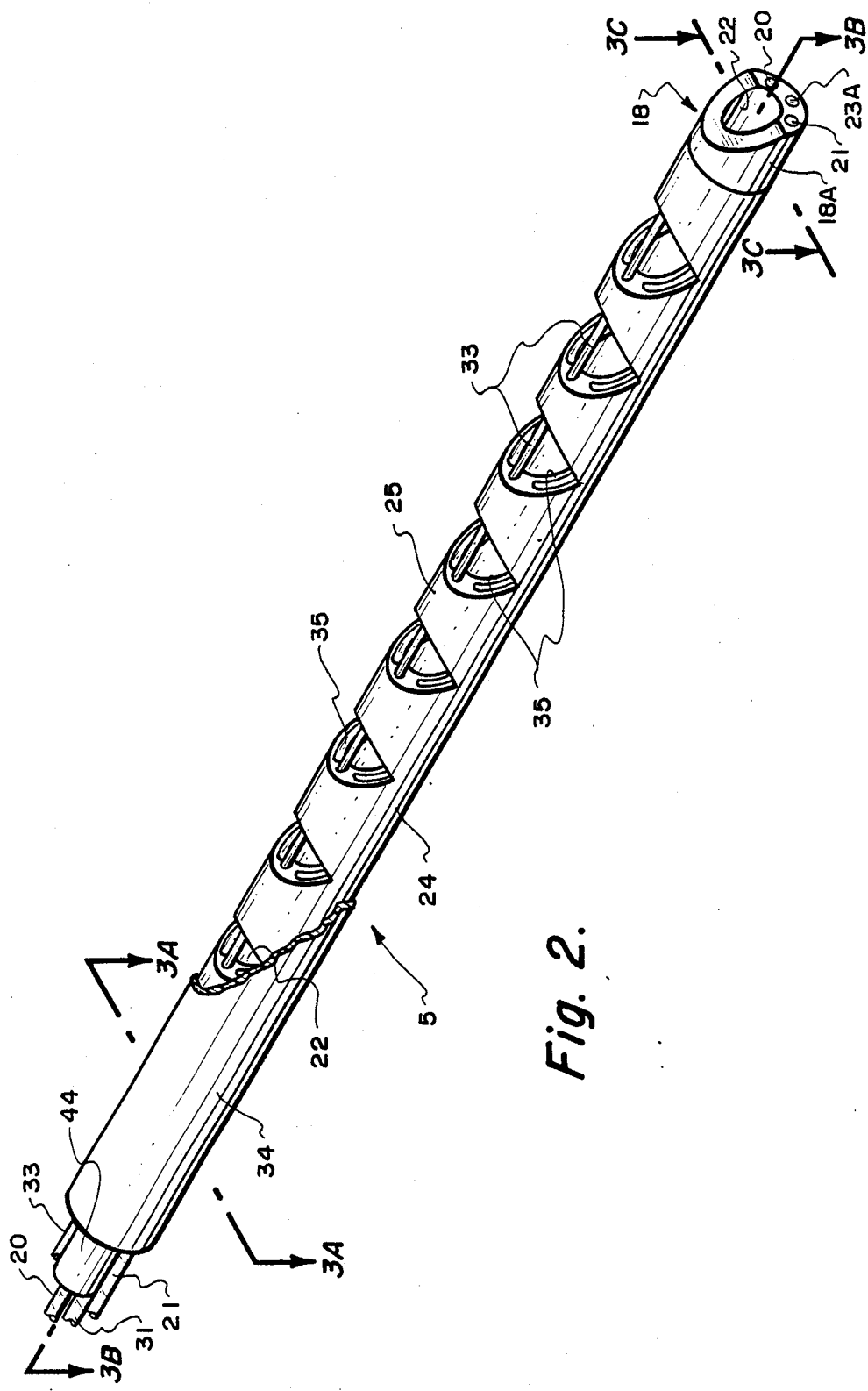
FIG. 2 is an isometric view of the shaft subassembly deflectable end segment.

Attention is now directed to FIG. 2 which illustrates a side elevation view of the deflectable end segment 5 of the shaft assembly 1 of FIG. 1A in its relaxed straight configuration. The distal tip 18 of segment 5 constitutes the exit point for the light pumped through the illumination fibers 20, 21 from lightpost 8 and a distal port for the working channel 22. It also provides a viewing window 23A where the image of the scene viewed is formed, by the distal end objective lens 23 (FIG. 3D). To further describe the deflectable end segment 5, cross sections taken at different positions and planes will be discussed in more detail.

Figure 3A:
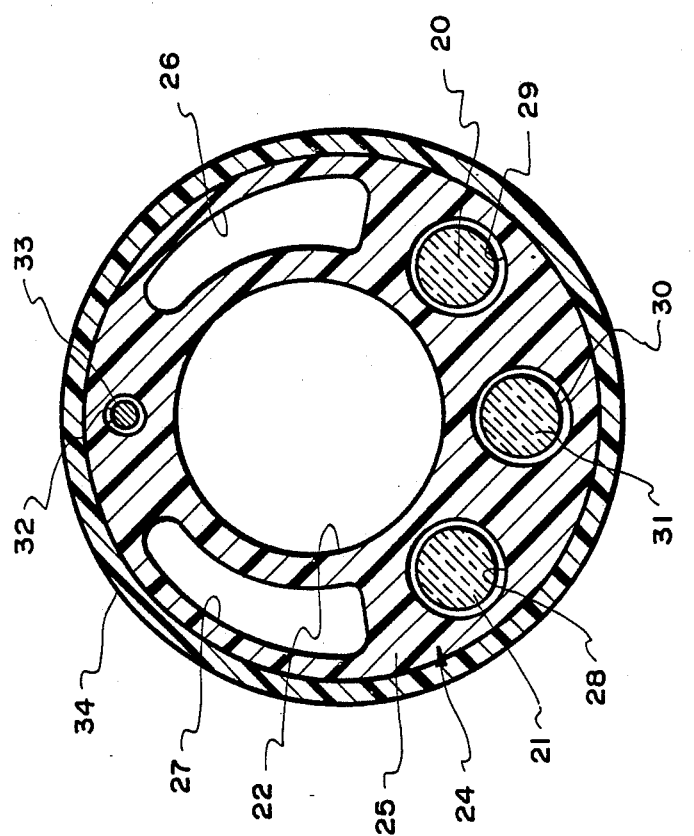
FIG. 3A is a lateral cross sectional view of the deflectable end segment taken substantially along the plane 3A—3A of FIG. 2.

FIG. 3A shows a lateral cross section view through section 3A-3A of the deflectable end segment 5 of FIG. 2. The structure essentially comprises a flexible multi-lumen, preferably thermoplastic tubing 24 (e.g. polyurethane of a moderate shore hardness). The relatively large central lumen 22 defines the working channel extending along the longitudinal axis of tubing 24. The tubing wall 25 may include empty channels 26, 27 extending along its length to facilitate flexibility of the deflectable end segment 5. One or more lumens 28, 29 are provided in the wall 25 extending along its length for respectively accommodating illumination fibers 20, 21. An additional lumen 30 extends through the tubing wall 25 along the length thereof for accommodating an imaging fiber bundle 31. In an alternative embodiment lumens 28, 29, 30 may be replaced by a singular kidney shaped lumen running parallel to the tubing longitudinal axis to accommodate simultaneously the imaging fiber 31 and illumination fibers 20, 21. A further lumen 32 extends through the tubing wall 25 along the length thereof and accomodates a pull wire 33, preferably formed of stainless steel. A tubular sheath 34, preferably of thermoplastic elastomeric material, tightly encases the assembled deflectable end segment 5 and extends throughout its length. The sheath 34 is of relatively lower shore hardness than the multi-lumen tubing 24. All the through lumens shown in FIG. 3A may deviate in shape from the circular geometry to another, e.g. elliptical, to accommodate the same overall functions of the deflectable end segment 5 of FIG. 2.

Figure 3B:
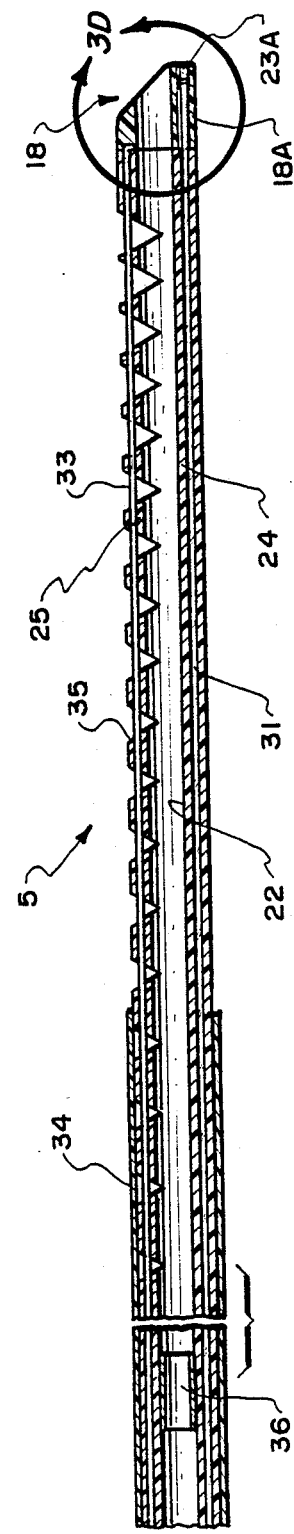
FIG. 3B is a longitudinal cross sectional view of the deflectable end segment taken substantially along the plane 3B—3B of FIG. 2.

Attention is now directed to FIG. 3B which shows a longitudinal cross section of the deflectable end segment 5. A series of discreet substantially aligned cutouts 35 are formed in the wall 25 of the multi-lumen tubing 24 and cut into the working channel 22. The dimensions of the cutouts are varied progressively along the length of the tubing 24 in a unique distribution. These cutouts are substantially triangular in a longitudinal plane containing the pull wire 33 and the imaging fiber bundle 31. The cutouts start relatively wide at the peripheral wall 25 of the tubing 24 and narrows down towards the tubing axis.

The distribution of the cutouts is structured to provide increased bendability of the tubing 24 progressively toward the distal end. In addition it causes a predetermined gradual deflection profile of the distal tip 17 in response to the pull wire 33 being pulled proximally. The cutouts geometry and distribution will also assure a continuous deflection of the distal tip 11 from 0 degrees to 180 degrees, within a plane defined by the straight longitudinal axis of the tubing 24, and the pull wire 33. As the deflection is initiated, the cutouts will progressively start to close. The imaging fiber 31, and the shore hardness of the multi-lumen tubing 24, possess enough stiffness to straighten out the deflected end segment from its deflected configuration when the force on the pull wire 33 is released at the handle. If deflection is required in any other plane, then the shaft subassembly 1 and handle subassembly 2 are rotated as a unit to rotate the deflectable end segment 5. The cutouts may alternatively have geometries with cross sections other than triangular e.g. rectangular, rounded, keyhole shape or a combination of some or all of the mentioned configurations. The cutouts separation and distribution with respect to either end of the tubing 24 may also vary to obtain the same function of the deflectable end segment 5. The working channel 22 in the deflectable end segment 5 and the conduit 4 are connected together to form a continuous path for the fluids and instruments, by means of a thin wall metal sleeve 18A which is securely bonded into the proximal end of the working channel 22 in the deflectable end segment 5.

Figure 3C:
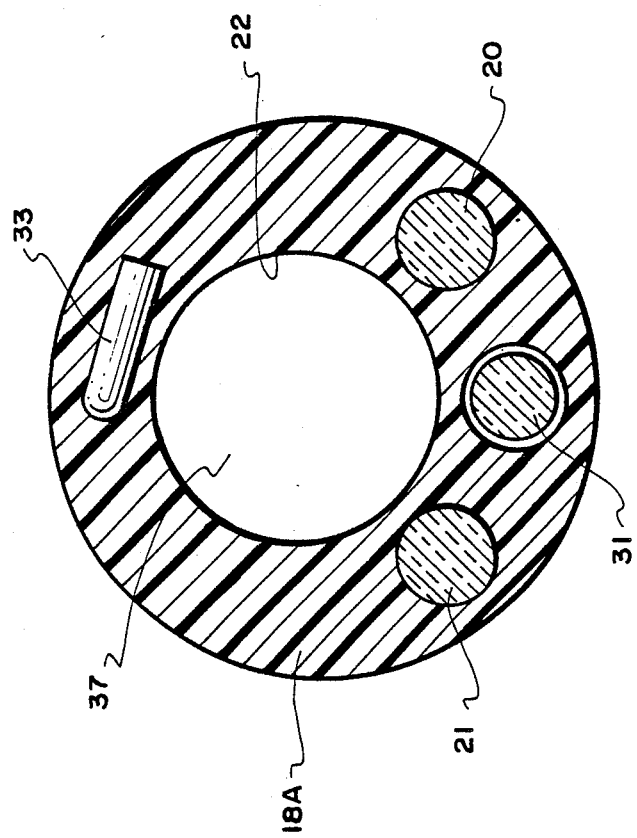
FIG. 3C is an exploded view of the end portion taken substantially along the plane 3C—3C of FIG. 2.
Figure 3D:
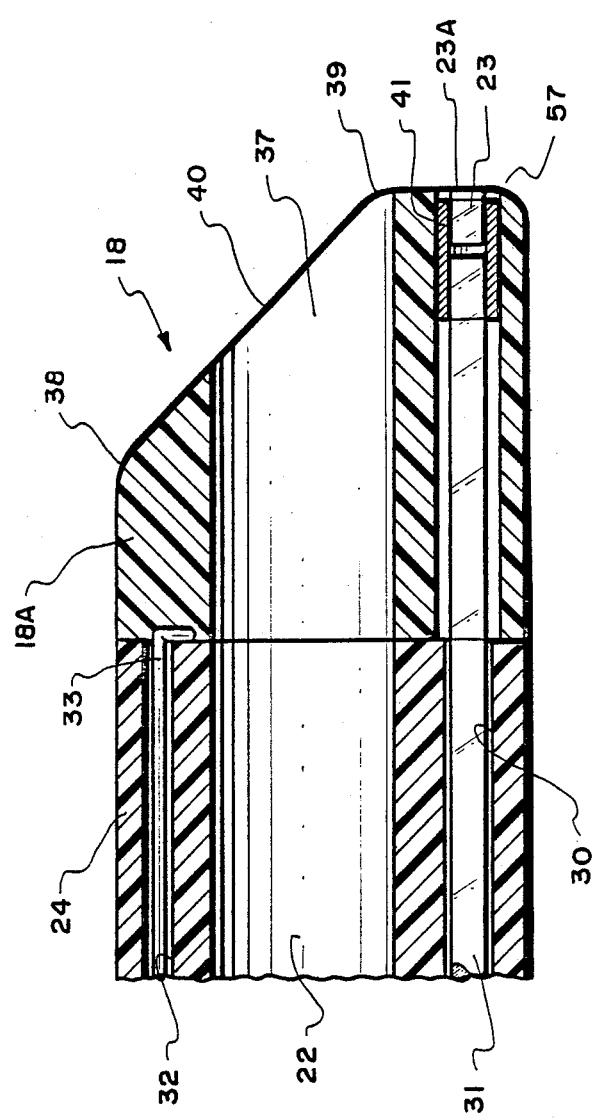
FIG. 3D is an exploded view of the distal tip of the deflectable end portion shown in FIG. 3B.

Attention is now directed to FIG. 3C which shows a lateral cross section view of the distal end 17 of the deflectable end segment. The structure of the distal tip 18 consists essentially of a relatively hard cured adhesive casing 18A which securely bonds the distal ends of the illumination fibers 20,21, imaging fiber 31 and pull wire 33 to the wall 25 of the multi-lumen tubing 24. The adhesive casing 18A is preferably shaped in a circular cross section, with smooth outside surface finish, to match that of the tubing 24 and to provide a smooth transition between the two segments. The adhesive casing 18A also provides a physical means to encase the illumination fibers 20, 21 and imaging fiber 31, and to secure the encasement to the distal end of the tubing 24. The walls of the adhesive casing 18A configures a hollow channel throughout its length to provide continuity of the working channel 22.

The pull wire 33 is terminated and bonded at the distal end of the tubing 24 (FIG. 3D) while the illumination fibers 20, 21, imaging fiber 31 and working channel 22 extend beyond the tubing 24/casing 18A junction. The magnified view (FIG. 3D) of the distal end shows that the surface of the distal tip is moderately angled e.g. 45 degrees, in a plane perpendicular to the plane containing the pull wire 33 and imaging fiber 31. The corners 38, 39 and the outer edge 40 of the distal tip are preferably rounded and polished to provide an atraumatic tip configuration to facilitate movement inside delicate relatively soft tissue surfaces, e.g. human organs. The atraumatic tip also provides a means to reduce the difficulty faced when inserting and passing the distal tip through tight orifices or constricted space e.g. seals of introducers and catheters which are normally used in clinical setups. As also illustrated in FIG. 3D, the imaging fiber 31 is terminated with a metal sleeve 41 which encapsulates at its distal end an objective lens 23, e.g. GRIN rod lens. The metal sleeve 41 provides a means to align the longitudinal optical axis of the imaging fiber bundle (to minimize coupling loss of the image light rays). The distal end of the imaging fiber bundle is preferably cut and polished in a plane of 90 degrees to its central axis prior to its assembly. The distal end of the imaging fiber 31 and the lens 23 are securely bonded with an optical adhesive which also bonds to the inner surface of the metal sleeve 41. The imaging fiber bundle, metal sleeve 41 and lens 23 form a lens subassembly 57, which is securely bonded to the distal tip 18. The front surface of lens subassembly 57 is placed flush against the distal end of the tip 18.

Figure 4A:
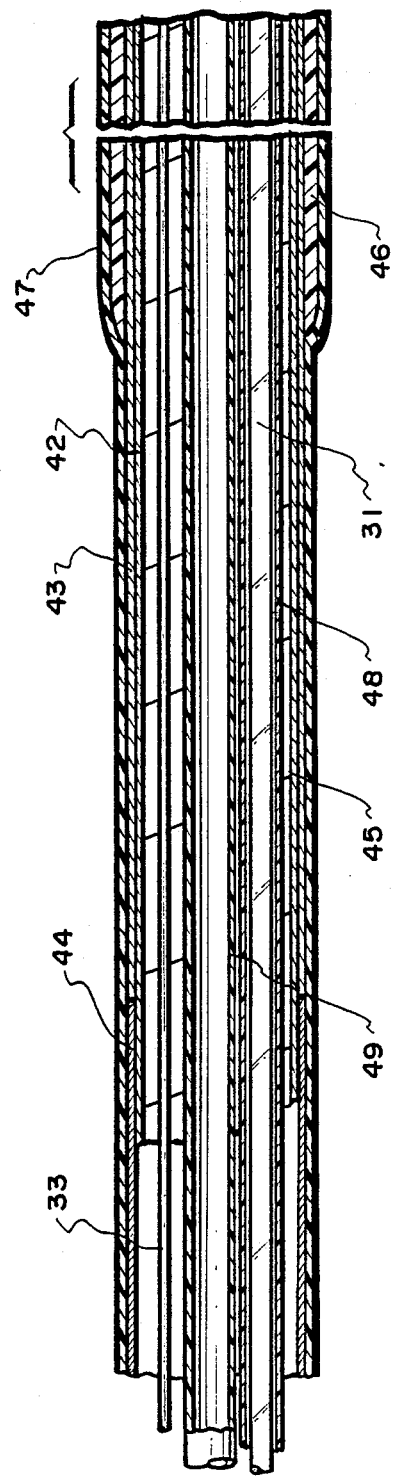
FIG. 4A is a longitudinal cross sectional view of the conduit in the shaft subassembly taken substantially along the plane 4A—4A in FIG. 1E.

Attention is now directed to FIG. 4A which shows a longitudinal cross section of the conduit 4 of the shaft subassembly The conduit 4 is comprised of a coil assembly including two tight wound flat metal ribbon coils 42, 43 counter wrapped tight against each other and around a common central longitudinal axis. The material of the coils is preferably spring tempered stainless steel. The distal end of the coil subassembly is terminated with a thin metal bushing 44 that partially encapsulates, and is bonded to the extended windings of the inner coil 42. The inside diameter of the distal end of the bushing 44 is large enough to slip over the proximal end of the deflectable end portion 17. Bushing 44 is securely bonded to the distal end of the conduit 4 and the proximal end of the flexible end segment 5.

The coil subassembly is covered by a dual layer of sturdy flexible tubular material preferably comprised of an elastomeric thermoplastic. The initial layer 46 covers the coil subassembly from the cone subassembly 6 extending distally along approximately half the length of the conduit 4. A second layer 47 covers the first layer 46 and extends from the cone subassembly 6 distally over the entire length of the coil subassembly ending at the distal end of the bushing 44. Both coverings 46, 47 have smooth inner and outer surfaces and exhibit high elastomeric properties to sustain 1 and support the stresses induced while flexing the coil subassembly. The coverings 46, and 47 enhance the transfer of torque from the proximal end of the endoscope to its distal end. In addition, they reinforce the strength of the conduit to withstand the stresses of tension, compression, pulling and torsion. A key feature of the coil subassembly is that it securely houses the imaging fiber, illumination fiber, working channel and pull wire throughout their length from the proximal end of the deflectable end segment 5 to the distal end of the cone subassembly 6.

Figure 4B:
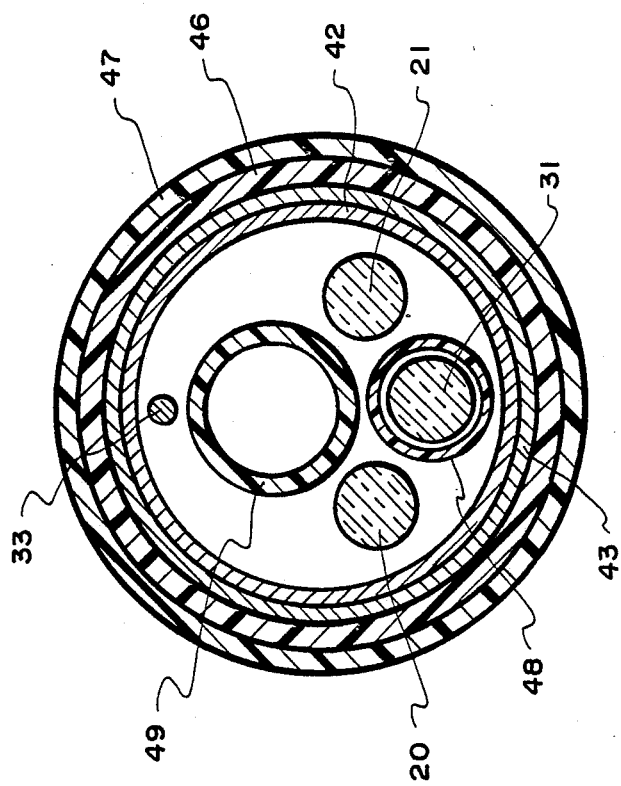
FIG. 4B is a lateral cross sectional view of the conduit in the shaft subassembly taken substantially along the plane 4B—4B in FIG. 1E.

Attention is directed now to FIG. 4B which illustrates a lateral cross section of the proximal portion of conduit 4, showing the lateral distribution of the imaging fiber bundle 31, imaging fiber conduit 48, illumination fibers 20, 21, pull wire 33 and working channel conduit 49. All these elements are loose in the inner space of the coil subassembly throughout its length except at the proximal end where they are securely bonded to the coil subassembly with an exception of the pull wire 33 which runs completely loose.

Figure 5:
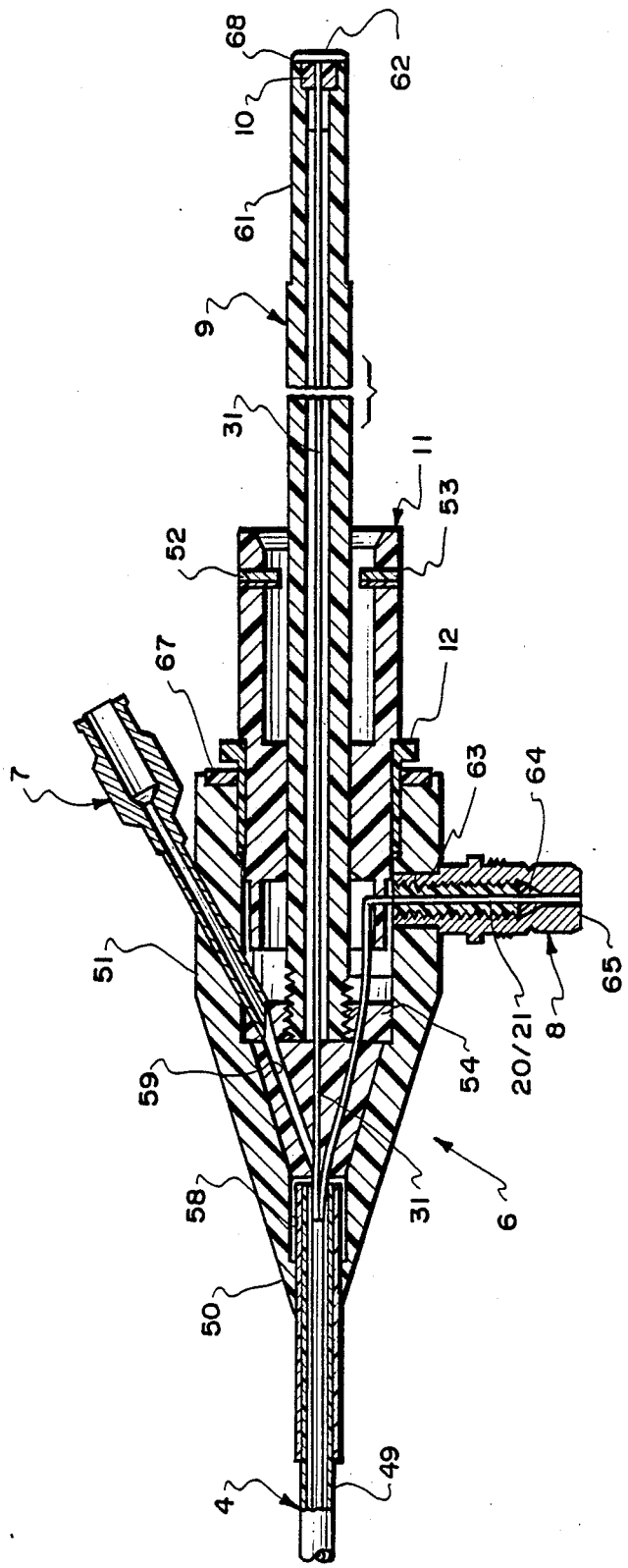
FIG. 5 is a longitudinal cross sectional view of the cone subassembly taken substantially along the plane 5—5 of FIG. 1C.

Attention is now directed to FIG. 5 which shows a longitudinal cross section of the cone subassembly 6. The cone subassembly includes a rigid structured housing 51 having a distal end 50 which receives the proximal end of conduit 4. The proximal end of conduit 4 is securely bonded within a trough channel 58. The cone subassembly 6 is essentially configured to accommodate the terminations of the imaging fiber bundle, illumination fibers, working channel and pull wire all of which emerge from the proximal end of the conduit 4. The cone subassembly 6 also provides a bayonet connector means by which the shaft subassembly 1 is attached to the handle subassembly 2 in a quick and reliable manner.

An extension of the working channel 59 joins the working channel conduit 49 which is securely bonded to the cone housing 51. The curvature in the working channel extension 59 provides a smooth passage for passing rigid and semi-rigid instruments. The imaging fiber bundle 31 is allowed to extend straight out from the proximal end of the conduit 4 and pass centrally through the hollow rigid post 9 and ferrule 10. The image fiber bundle is securely bonded to ferrule 10, which provides mechanical protection for the fiber end which is cut and polished 90 degrees to the proximal end surface of the ferrule 10. The length of the rigid post 9 and subsequently the length of the image fiber bundle 31 contained therein is directly related to the proper imaging (focus) distance between the ferrule 10 end surface and the viewing lens located within the handle subassembly 2. The concentricity of the proximal end of post 9 is maintained to provide for proper and efficient centering of the polished end surface 62 of the image fiber bundle 31 with respect to the viewing lens in the handle subassembly 2 when the shaft subassembly 1 and handle subassembly 2 are engaged.

Illumination fibers 20, 21 are routed from the proximal end of the conduit 4 through an opening 63 in the lateral side wall of the cone housing 51 and terminate in the light post adapter 8. The light post adapter 8 is preferably configured to be compatible with industry standard fittings. The illumination fibers 20, 21 are securely bonded with an hardcure adhesive 64 to the light post adapter 8. The illumination fibers 20, 21 are then cut and polished at a 90 degree angle to the lateral end surface 65 of the illumination post 8.

Figure 6A:
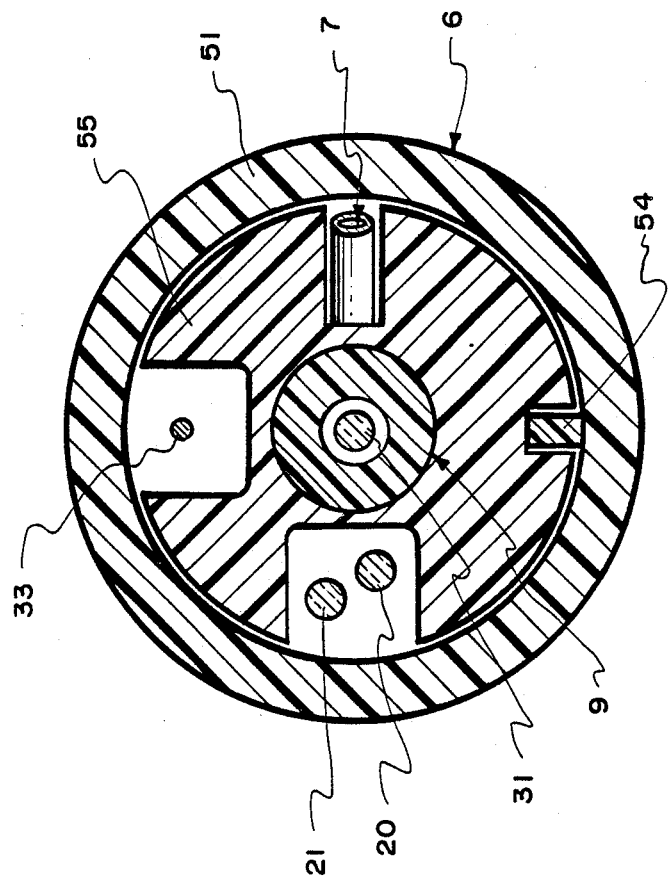
FIG. 6A is a lateral cross sectional view of the cone subassembly taken substantially along the plane 6A—6A of FIG. 1A.

The pull wire 33 is passed through the central area of the cone subassembly 6 and is securely attached and bonded to the movable lifter 11. FIG. 6A shows the location of the pull wire as i passes centrally through the cone assembly 6. The pull wire 33 is offset to the side of the central axis of the cone subassembly in a plane perpendicular to the plane defined by the illumination post 8., the working channel port 7 and the central longitudinal axis of the cone subassembly. Diametrically opposite to the pull wire, on the lateral inside surface of the cone subassembly is a location key 54 which extends from the laterally centermost portion of the cone subassembly proximally to the side of lifter 11. The key function is to maintain alignment of the lifter 11 with respect to the illumination post 8 and working channel port 7. The key 54 also prevents rotational movement of lifter 11 about the longitudinal centerline of the cone subassembly. Located at the proximal end of the lifter 11 are two radially internally protruding pins 52, 53 (FIG. 5) which engage with mating slots in the deflection control mechanism on the handle subassembly 2.

By rotating the deflection control ring 16 on the handle subassembly 2, the lifter 11 will travel smoothly and gradually in a longitudinal path pulling directly behind it the pull wire 33 which in turn causes the distal end segment 5 to bend. The cone subassembly 6 is configured with a bayonet connector means 12 that can be quickly coupled to its counterpart on the handle subassembly 2. Set in a recess of the proximal end of the rigid cone 51 is a elastomeric circular seal 67 which is squeezed between the distal end of the handle subassembly 2 and proximal end of the shaft subassembly 1 when the two subassemblies are mated.

FIG. 6A shows the housing 51 wall structure which surrounds a key 54, the imaging fiber, illumination fibers, working channel and pull wire, as they emerge out of the proximal end of the cone housing 51 to their corresponding terminals These elements are bonded to the inside wall of the housing 51 within a central base element 55. In addition, the rigid post 9 is securely threaded and bonded to the central portion of the housing 51.

Figure 6B:
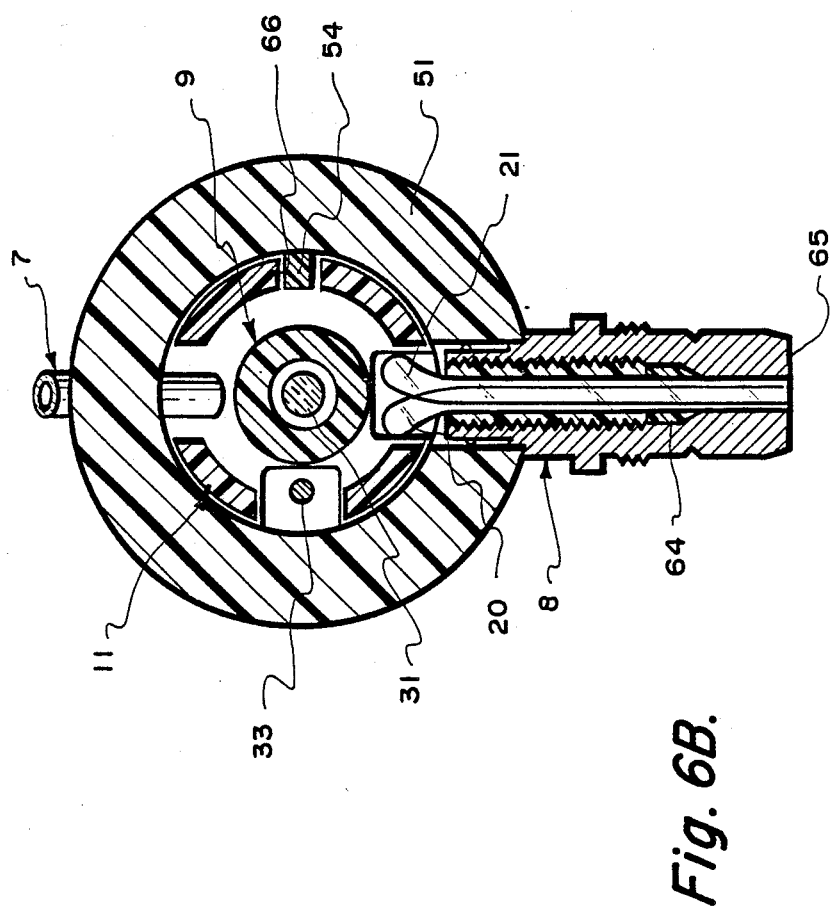
FIG. 6B is a lateral cross sectional view of the cone subassembly taken substantially along the plane 6B—6B in FIG. 1E.

Attention is now directed to FIG. 6B which shows the extension of the key 54 into a cutout 66 in the lateral wall of the lifter 11. The mating of key 54 with cutout 66 guarantees alignment of the lifter 11 with respect to the previously mentioned components of the cone subassembly and prevents rotation of the lifter 11.

Figure 6C:
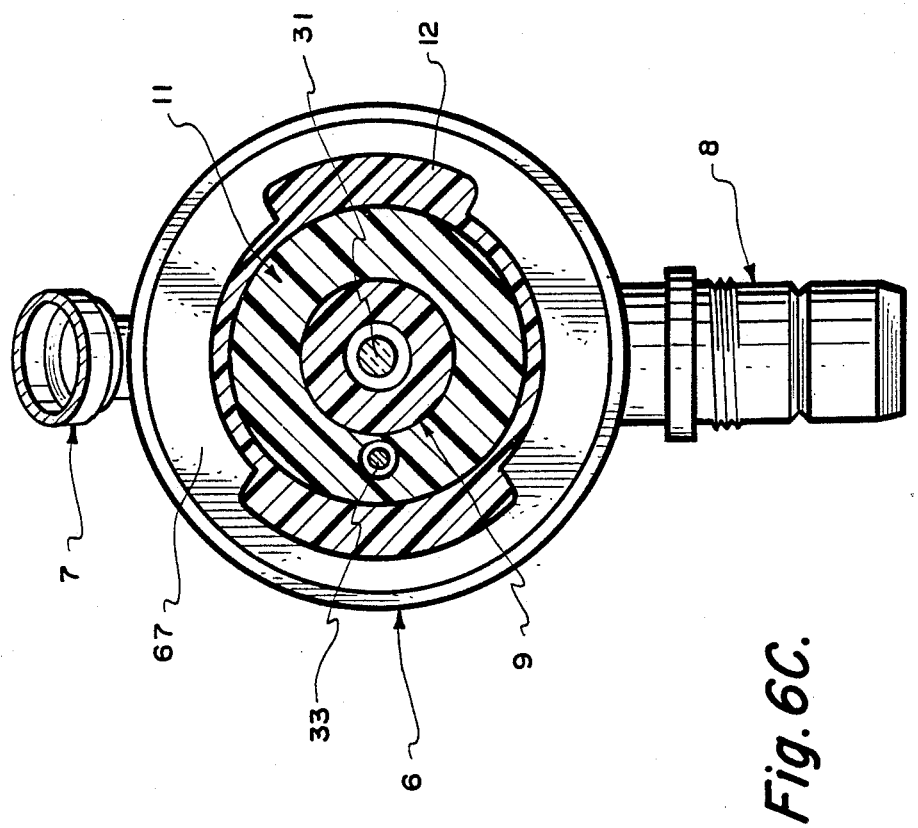
FIG. 6C is a lateral cross sectional view of the cone subassembly taken substantially along the plane 6C—6C in FIG. 1A.

FIG. 6C shows the location of the pull wire within the body of the axially movable lifer 11. The pull wire is securely bonded to lifter 11 such that any axial movement of the lifter 11 proximally or distally causes a subsequent pull or release of the pull wire 33. Also shown in FIG. 6C is a cutaway of the male bayonet connector 12 which is to be mated with a female bayonet connector located on the handle subassembly 2.

Figure 7:
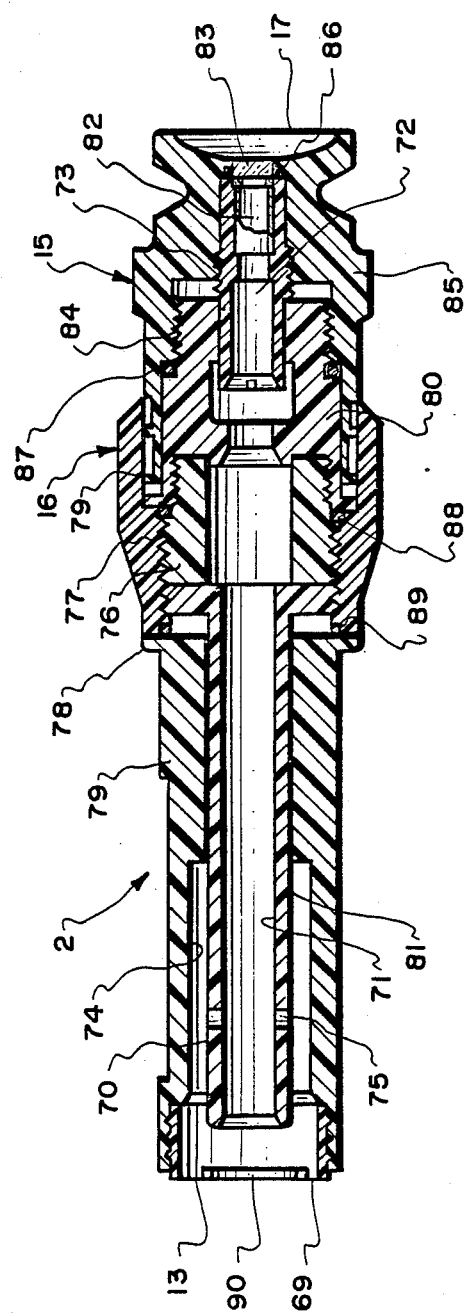
FIG. 7 is a longitudinal cross sectional view of the handle subassembly taken substantially along the plane 7—7 in FIG. 1B.

Attention is now directed to FIG. 7 which shows a cross section of the handle subassembly 2. In order to connect the shaft subassembly 1 to the handle subassembly 2, the fiber post 9 is inserted into the connector cavity 71 of the handle subassembly 2 and slid proximally until the concentric portion 61 of the post 9 engages the optical module 72 of the handle subassembly 2. Concurrent with this engagement, the male bayonet projections 12 on the shaft subassembly are inserted into recesses between the female bayonet projections 90 on the handle subassembly. The pins 52, 53 in the lifter 11 of the shaft subassembly are slid along longitudinal slots in the shuttle 70 of the handle subassembly A rotation of the shaft subassembly 1 with respect to the handle subassembly 2 results in the locking of the male and female bayonet connectors 12, 90 and the engagement of the lifter pins 51, 52 within lateral slots 74 and 75 on the shuttle. By so structurally interconnecting, the shaft and handle subassemblies are automatically operationally connected enabling the user to manipulate the control ring 16 on the handle subassembly for purposes of deflecting the deflectable end segment 5. The user may also manipulate the distance between the lens in the optics module 73 and the proximal end of the image fiber bundle 62 by turning the focusing ring 15. The male bayonet connectors 12 on the shaft subassembly 1 and the female bayonet connectors 90 on the handle subassembly 2 are provided with slight angles such that when engaged the handle subassembly and the shaft subassembly are pulled together. The elastomeric seal 67 then becomes sandwiched between the proximal end of the cone subassembly 6 and the distal end 69 of the handle subassembly. This sandwiching results in the secure locking together of the two subassemblies.

The proximal end of the shuttle 71 is threaded with external threads 76 which are mated with internal threads 77 of the deflection control ring 16. The deflection control ring 16 is axially constrained between flanges 78 and 79. Therefore a rotation of the deflection control ring causes a longitudinal movement of the lifter 11 which results in displacement of the pull wire 33 and subsequently a bending of the deflectable end segment 5. The pitch angle of the threads 76, 77 is chosen to allow for a 0–180 degree bend of the segment 5 with less than a single rotation of the deflection control ring 16. The pitch angle is also chosen to minimaize the amount of torque necessary to rotate the deflection control ring thus providing enough axial tension on the pull wire to effect deflection of distal end portion 5 in a discrete or continuous fashion. FIG. 7 illustrates an embodiment in which a pitch angle of 8 degrees is utilized, though a lesser or greater angle could be tolerated. It is appreciated that alternative embodiments could utilize other structures, e.g. a cam as used in zoom optical lens, in place of the threaded deflection control mechanism 16 just described.

An optics module 73 with a lens 82 and plane window 83 is provided in the handle subassembly 2 for focusing on the polished surface 62 of the image fiber bundle 31. The optical module 73 is provided with a concentric lumen 72 which when mated with the concentric proximal end 61 of the post 9 ensures alignment of the optical fiber bundle 31 with the optical lens 82. The optical module 73 is encased within focusing ring 15. The focusing ring 15 is internally threaded 85. The internal threads 85 are mated with external threads 84 on the union 80 between the focusing mechanism and the deflection mechanism. Rotation of the focusing ring with respect to the handle 79 results in the longitudinal displacement of the optics module with respect to the polished proximal end of the image fiber bundle 62. It is appreciated that alternative embodiments could use other structures, e.g. a cam mechanism for the longitudinal movement of the optics module.

Seals 86, 87, 88 and 89 are provided to protect the interior of the handle subassembly from water and vapors which might otherwise compromise the handle subassembly during use or sterilizations.

From the foregoing, it should now be appreciated that an improved endoscope has been disclosed herein comprised of a reusable handle subassembly and a shaft subassembly which can be readily attached and detached from the handle subassembly. The connection between the two subassemblies is characterized by a bayonet coupling which not only structurally connects the two subassemblies but which automatically operationally interconnects a shuttle mechanism in the handle subassembly with a lifter in the shaft subassembly for enabling a user to readily pull on a pull wire extending through the shaft subassembly to a deflection end segment. The shaft subassembly is further characterized by the inclusion of inherent resiliency and tensioning so as to normally cause the deflectable end segment to be aligned with the rest of the shaft subassembly when line pull wire is in a relaxed state. The deflectable end segment is characterized by a series of cutouts whose dimensions progressively change from the distal to the proximal end to facilitate gradual and smooth bending of the deflectable end segment.

We claim:

1. A shaft subassembly adapted for attachment to a handle subassembly to form an endoscope, said shaft subassembly comprising:

elongated conduit means defining a nominal axis and including a deflectable end segment having proximal and distal ends, said end segment defining a viewing surface at said distal end and further comprising:

an elongated tubular member comprised of a peripheral wall surrounding a channel extending the length thereof;

a plurality of aligned cutouts formed in said peripheral wall spaced along the length thereof, each of said cutouts extending radially inward from the outer surface of peripheral wall, said cutouts having dimensions which progressively vary with increasing distance from said distal end;

a lumen formed in said peripheral wall extending the length of said tubular member; and a pull wire extending through said lumen having a distal end anchored to said tubular member proximate to said viewing surface and radially spaced form said axis.

2. The shaft subassembly of claim 1 further including sheath means mounted on said tubular member around said peripheral wall outer surface for closing said cutouts.

3. The shaft subassembly of claim 2 wherein said pull wire passes through said cutouts.

4. The shaft subassembly of claim 1 further including resilient means for normally biasing said tubular member into substantial alignment with said conduit means axis.

5. The shaft subassembly of claim 4 further including means secured to said pull wire proximal end for pulling said pull wire through said lumen toward said proximal end for progressively collapsing said cutouts to deflect said tubular member distal end out of alignment with said conduit means axis.

6. The shaft subassembly of claim 1 further including an elongated image fiber extending through said conduit means and end segment.

7. The shaft subassembly of claim 1 wherein said conduit means includes an intermediate section having said end segment connected to the distal end thereof and a connector subassembly connected to the proximal end thereof;

said intermediate section comprising a hollow tubular structure formed by at least one flat ribbon coil.

8. The shaft subassembly of claim 7 wherein said connector subassembly includes bayonet connector means for interconnecting said shaft subassembly to said handle subassembly.

9. An endoscope comprising:

handle subassembly means including user manipulable control means;

shaft subassembly means including elongated tubular means defining a nominal axis;

a pull wire extending through said tubular means for limited reciprocal movement parallel to said nominal axis; and mating attachment means respectively mounted on said handle subassembly means and said shaft subassembly means for structurally interconnecting them and for concurrently operationally connecting said control means to said pull wire.

10. The endoscope of claim 9 wherein:

said handle subassembly means further includes shuttle means mounted for reciprocal linear movement in response to manipulation of said control means; and wherein said shaft subassembly means further includes lifter means for automatically connecting said pull wire to said shuttle means when said handle subassembly means and said shaft subassembly means are structurally interconnected.

11. The endoscope of claim 10 wherein said attachment means includes:

bayonet mounting means on said handle subassembly means;

bayonet connector means on said shaft subassembly means configured to attach to said bayonet mounting means only when in a unique orientation relative thereto; and wherein said lifter means automatically connects to said shuttle means when said connector means is in said unique orientation relative to said mounting means.

12. The endoscope of claim 11 wherein said shaft subassembly means includes a tubular segment located at one end thereof remote from said connector means, said tubular segment defining a distal tip;

a lumen extending through said tubular segment; said pull wire extending through said lumen and having a distal end anchored to said distal tip.

13. The endoscope of claim 12 wherein said tubular segment is configured so as to readily bend when said pull wire is pulled in a direction away from said distal tip;

said tubular segment comprising a peripheral wall surrounding a central channel extending the length thereof; and a plurality of aligned cutouts formed in said peripheral wall spaced along the length thereof, each of said cutouts extending radially inward from the outer surface of said peripheral wall, said cutouts having dimensions which progressively vary with increasing distance from said distal tip.

14. The endoscope of claim 13 further including sheath means mounted on said tubular segment around said peripheral wall outer surface for closing said cutouts.

15. The endoscope of claim 14 further including resilient means for normally biasing said tubular segment into alignment with said shaft subassembly means axis.

16. The endoscope of claim 9 wherein said shaft subassembly means includes an elongated image fiber extending therethrough substantially parallel to said axis, said image fiber having a first end terminating substantially coincident with the distal end of said shaft subassembly and a second end extending beyond the proximal end of said shaft subassembly;

said handle subassembly means including an eyepiece; and wherein said eyepiece and image fiber second end are substantially aligned when said handle subassembly means and said shaft subassembly means are interconnected.

* * * * *